US00PP11136P

United States Patent [19]

Kordes

[11] Patent Number: Plant 11,136

[45] Date of Patent: Nov. 30, 1999

[54] MINIATURE ROSE PLANT NAMED 'KORLINIK'

[75] Inventor: Wilhelm Kordes, Sparrieshoop, Germany

[73] Assignee: Bear Creek Gardens, Inc., Medford, Oreg.

[21] Appl. No.: 09/046,115

[22] Filed: Mar. 20, 1998

[51] Int. Cl.[6] ..... A01H 5/00

[52] U.S. Cl. ..... Plt./118

[58] Field of Search ..... Plt./118, 125

*Primary Examiner*—Howard J. Locker

*Attorney, Agent, or Firm*—Klarquist Sparkman Campbell Leigh & Whinston, LLP

[57] ABSTRACT

A miniature rose plant having rapid rooting of softwood cuttings; compact, well-branched growth; long lasting, bright yellow flowers; and good shelf life as a pot rose.

1 Drawing Sheet

The present invention relates to a new and distinct variety of rose plant of the miniature class which was originated by me by crossing an unnamed seedling, (not patented), the parentage of which is unnamed, with 'KORdaba' (U.S. Plant Pat. No. 9,116).

The primary objective of this breeding was to produce a new rose variety having a compact, well branched growth habit, the ability to root rapidly from softwood cuttings, to grow rapidly and flower quickly in a 10 cm pot, to have good shelf life, and to have flowers that hold their color without fading. The objective was substantially achieved, along with other desirable improvements, as evidenced by the following unique combination of characteristics that are outstanding in the new variety and that distinguish it from its parents, as well as from all other varieties of which I am aware:

1. Long lasting, bright yellow flowers;
2. Compact, well branched growth;
3. Rapid rooting from softwood cuttings;
4. Good shelf life as a 10 cm pot rose.

'KORlinik' can allso be grown as an attractive miniature garden rose.

Asexual reproduction of this new variety by cuttings, as performed at Somis and Wasco, Calif. and Spaarieshoop, Germany, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptrions using terminology in accordance with The Royal Horticultural Society (London) Colour Chart, except where ordinary dictionary significance of color is indicated.

Parentage:

*Seed parent.*—Unnamed seedling (not patented), the parentage of which is unnamed.

*Pollen parent.*—'KORdaba' (U.S. Plant Pat. No. 9,116).

Classification:

*Botanical.*—*Rosa hybrida.*

*Commercial.*—Miniature.

FLOWER

Observations made from specimens grown in a greenhouse environment at Somis, Calif. and Sparrieshoop, Germany.

Blooming habit: Continuous

Bud:

*Size.*—3;4" long when the petals start to unfurl.

*Form.*—Long, pointed ovoid.

*Color.*—When sepals first divide, bud color is Yellow Group 13A. When half blown, the upper sides of the petals are Yellow Group 13A and the lower sides of the petals are Yellow Group 13A.

*Sepals.*—Color: Green Group 138B. Surface texture: Covered in fine hairs. There are three lightly appendaged sepals. There are two unappendaged sepals with hairy edges.

*Receptacle.*—Color: Green Group 137C. Shape: Funnel. Size: Medium (5/16"×3/8"). Surface: Smooth.

*Peduncle.*—Length: Short (2"). Surface: Smooth, with a few small glands. Color: Medium green. Strength: Stiff, erect.

Bloom:

*Size.*—Small. Average open size is 1½" to 1¾".

*Borne.*—Singly, several together in clusters of 3 to 5 having pyramidal shape.

*Stems.*—Short (6–8"), strong.

*Form.*—When first open: High centered. Permanence: Outer petals curl back, quill fashion.

*Petalage.*—Number of petals under normal conditions: 25–30.

*Color.*—The upper sides of the petals are Yellow Group 13A. The reverse sides of the petals are Yellow Group 13A. The bases of the petals have no noticeable color change. The major color on the upper sides is Yellow Group 13A.

*Variegations.*—Occasional greenish white streak on the guard petals.

*Discoloration.*—There is no color change through day nine on the plant. Then the individual bloom will fade to Yellow Group 13C before petal fall at day eleven or twelve.

*Fragrance.*—Slight.

Petals:

*Texture.*—Thick.

*Shape.*—Deltoid.

*Form.*—Tips slightly recurved, edges slightly quilled.

*Arrangement.*—Imbricated. Petaloids in the center are few.

*Persistence.*—Petals drop off cleanly before drying.

*Lastingness.*—On the plant: Long (10–11 days). As a cut flower: very long (12–13 days).

Reproductive parts:

*Anthers.*—Size: Medium. Quantity: Many. Color: Yellow. Arrangement: Regular around styles.

*Filaments.*—Color: Yellow.
*Pollen.*—Color: Gold yellow.
*Styles.*—Color: Greenish white.
*Stigmas.*—Color: Greenish white.

Plant:
*Form.*—Bush.
*Growth.*—Vigorous; dwarf; upright; branching: Height of mature plant is twenty-four inches, width is eighteen inches, if grown as a miniature garden rose outdoors.

Foliage: Number of leaflets on normal mid-stem leaves: Five or seven.
*Size.*—Small (3½"×2").
*Quantity.*—Abundant.
*Color.*—New foliage: Upper and lower sides: Greyed-Orange 178A, but very quickly turns Yellow-Green Group 146C on upper surface and 146D on lower surface. Old foliage: Upper side: Green Group 139A Lower side: Green Group 139C.

Leaflets:
*Shape.*—Pointed oval.
*Texture.*—Upper side: Leathery, glossy.
*Edge.*—Serrated.
*Serration.*—Single, small.
*Petiole rachis.*—Color: Green.
*Petiole underside.*—Smooth with occasional prickles.
*Stipules.*—Medium (⅜"–½"); serrated, bearded.
*Disease resistance.*—Resistant to mildew under normal growing conditions at Somis, Calif.

Wood:
*New wood.*—Color: Light Green. Bark: Smooth.
*Old wood.*—Color: Green. Bark: Smooth.

Prickles:
*Quantity.*—On main canes from base: Ordinary. On laterals from main canes: Ordinary.
*Form.*—Medium; hooked downward.
*Color when young.*—Green.

Small prickles:
*Quantity.*—On main stalks: None. On laterals: None.

I claim:

1. A new and distinct variety of rose plant of the miniature rose class, substantially as herein shown and described, characterized particularly by the rapid rooting of softwood cuttings; its compact, well-branched growth; long lasting, bright yellow flowers; and good shelf life as a pot rose.

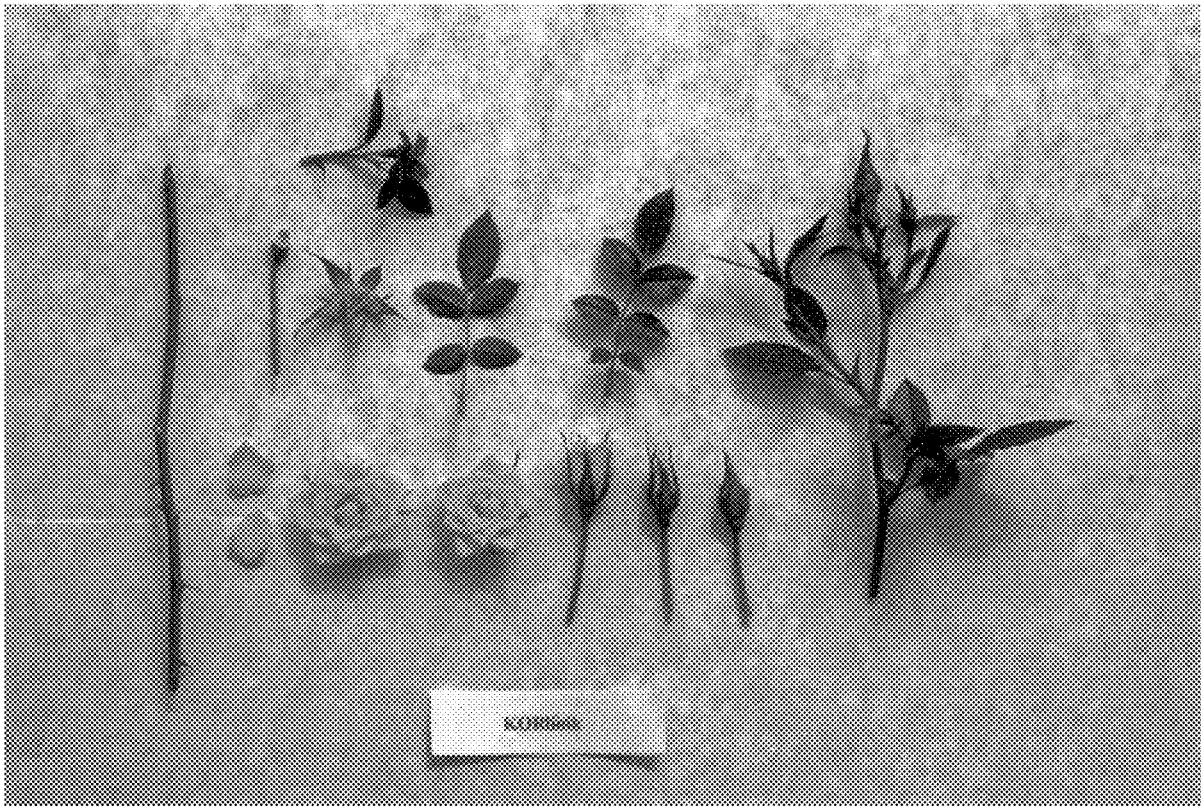

* * * * *